(12) United States Patent
Finley et al.

(10) Patent No.: US 10,729,552 B2
(45) Date of Patent: *Aug. 4, 2020

(54) IMPLANT CONFIGURED FOR HAMMERTOE AND SMALL BONE FIXATION

(71) Applicant: Biomet C.V., Warsaw, IN (US)

(72) Inventors: Adam Finley, Winona Lake, IN (US);
Jacy C. Hoeppner, Warsaw, IN (US);
Kevin T. Stone, Winona Lake, IN (US)

(73) Assignee: Biomet C.V., Warsaw, IN (US)

( * ) Notice: Subject to any disclaimer, the term of this patent is extended or adjusted under 35 U.S.C. 154(b) by 228 days.

This patent is subject to a terminal disclaimer.

(21) Appl. No.: 15/686,286

(22) Filed: Aug. 25, 2017

(65) Prior Publication Data

US 2017/0354509 A1 Dec. 14, 2017

Related U.S. Application Data (63) Continuation of application No. 14/661,250, filed on Mar. 18, 2015, now Pat. No. 9,763,800.

(51) Int. Cl.
*A61F 2/42* (2006.01)
*A61B 17/064* (2006.01)
(Continued)

(52) U.S. Cl.
CPC ........ *A61F 2/4225* (2013.01); *A61B 17/0642* (2013.01); *A61B 17/56* (2013.01);
(Continued)

(58) Field of Classification Search
CPC .................................................... A61F 2/4225
See application file for complete search history.

(56) References Cited

U.S. PATENT DOCUMENTS

| 3,855,638 A | 12/1974 | Pilliar |
| 4,708,799 A | 11/1987 | Gerlach et al. |

(Continued)

FOREIGN PATENT DOCUMENTS

| AU | 748575 B2 | 6/2002 |
| CN | 101166485 | 4/2008 |

(Continued)

OTHER PUBLICATIONS

"International Application Serial No. PCT/US2016/023094, International Preliminary Report on Patentability dated Sep. 28, 2017", 11 pgs.

(Continued)

*Primary Examiner* — Bruce E Snow
*Assistant Examiner* — Melissa A Hoban
(74) *Attorney, Agent, or Firm* — Schwegman Lundberg & Woessner, P.A.

(57) ABSTRACT

An implant configured for fusing a first bone segment and a second bone segment during an operative procedure and constructed in accordance to one example of the present disclosure includes an implant body, a first bone interfacing portion and a second bone interfacing portion. The implant body can extend longitudinally between an insertion end and an opposite end. The first bone interfacing portion can be provided on the implant body and be configured to be implanted relative to the first bone segment. The second bone interfacing portion can be provided on the implant body and be configured to be implanted relative to the second bone segment. The first and second bone interfacing portions can be inserted dorsally into the first and second bone segments, respectively.

16 Claims, 8 Drawing Sheets

(51) Int. Cl.
*A61B 17/84* (2006.01)
*A61B 17/56* (2006.01)
(52) U.S. Cl.
CPC ...... *A61B 17/84* (2013.01); *A61B 2017/0647* (2013.01); *A61F 2002/4233* (2013.01)

(56) References Cited

U.S. PATENT DOCUMENTS

| | | |
|---|---|---|
| 4,853,137 A | 8/1989 | Ersson |
| 5,015,248 A | 5/1991 | Burstein et al. |
| 5,075,222 A | 12/1991 | Hannum et al. |
| 5,359,032 A | 10/1994 | Dayer et al. |
| 5,443,516 A | 8/1995 | Albrektsson et al. |
| 5,571,418 A | 11/1996 | Lee et al. |
| 5,585,007 A | 12/1996 | Antanavich et al. |
| 5,599,558 A | 2/1997 | Gordinier et al. |
| 5,707,331 A | 1/1998 | Wells et al. |
| 5,788,662 A | 8/1998 | Antanavich et al. |
| 5,792,450 A | 8/1998 | Wilson et al. |
| 5,842,477 A | 12/1998 | Naughton et al. |
| 6,063,297 A | 5/2000 | Antanavich et al. |
| 6,096,728 A | 8/2000 | Collins et al. |
| 6,214,338 B1 | 4/2001 | Antanavich et al. |
| 6,287,558 B1 | 9/2001 | Lanza et al. |
| 6,337,072 B1 | 1/2002 | Ford et al. |
| 6,342,076 B1 | 1/2002 | Lundborg |
| 6,398,972 B1 | 6/2002 | Blasetti et al. |
| 6,533,454 B1 | 3/2003 | Kaikkonen et al. |
| 6,599,873 B1 | 7/2003 | Sommer et al. |
| 6,623,472 B1 | 9/2003 | Reincke et al. |
| 6,649,072 B2 | 11/2003 | Brandt et al. |
| 6,713,246 B1 | 3/2004 | Reinecke et al. |
| 6,758,849 B1 | 7/2004 | Michelson |
| 6,759,188 B2 | 7/2004 | Reinecke et al. |
| 6,790,371 B2 | 9/2004 | Dolecek |
| 6,811,777 B2 | 11/2004 | Mishra |
| 6,835,377 B2 | 12/2004 | Goldberg et al. |
| 6,905,612 B2 | 6/2005 | Dorian et al. |
| 7,011,852 B2 | 3/2006 | Sukavaneshvar et al. |
| 7,166,283 B2 | 1/2007 | Tsuji et al. |
| 7,179,391 B2 | 2/2007 | Leach et al. |
| 7,223,346 B2 | 5/2007 | Dorian et al. |
| 7,291,175 B1 | 11/2007 | Gordon |
| 7,374,678 B2 | 5/2008 | Leach et al. |
| 7,465,293 B2 | 12/2008 | Reinecke et al. |
| 7,470,371 B2 | 12/2008 | Dorian et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |
| 7,867,765 B2 | 1/2011 | Faustman et al. |
| 7,901,344 B2 | 3/2011 | Yoo |
| 7,901,584 B2 | 3/2011 | Dorian et al. |
| 7,914,689 B2 | 3/2011 | Higgins et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,202,539 B2 | 6/2012 | Behnam et al. |
| 8,753,690 B2 | 6/2014 | Higgins et al. |
| 8,784,457 B2 | 7/2014 | Graham |
| 9,763,800 B2 | 9/2017 | Finley et al. |
| 10,166,022 B2 | 1/2019 | Early et al. |
| 2001/0053764 A1 | 12/2001 | Sims et al. |
| 2002/0077276 A1 | 6/2002 | Fredeking et al. |
| 2002/0119179 A1 | 8/2002 | Rezania et al. |
| 2003/0040750 A1 | 2/2003 | Stoffella |
| 2003/0055511 A1 | 3/2003 | Schryver et al. |
| 2003/0091536 A1 | 5/2003 | Frisbie et al. |
| 2003/0099650 A1 | 5/2003 | Ho et al. |
| 2003/0138910 A1 | 7/2003 | Reinecke et al. |
| 2003/0139746 A1 | 7/2003 | Groiso |
| 2003/0194397 A1 | 10/2003 | Mishra |
| 2003/0205538 A1 | 11/2003 | Dorian et al. |
| 2004/0092937 A1 | 5/2004 | Criscuolo et al. |
| 2004/0120942 A1 | 6/2004 | Mcginnis et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0084962 A1 | 4/2005 | Simon |
| 2005/0100536 A1 | 5/2005 | Mishra |
| 2005/0109716 A1 | 5/2005 | Leach et al. |
| 2005/0124993 A1 | 6/2005 | Chappuis |
| 2005/0152905 A1 | 7/2005 | Omoigui |
| 2005/0186120 A1 | 8/2005 | Dorian et al. |
| 2005/0196874 A1 | 9/2005 | Dorian et al. |
| 2005/0197293 A1 | 9/2005 | Mellis et al. |
| 2006/0046960 A1 | 3/2006 | Mckay et al. |
| 2006/0051865 A1 | 3/2006 | Higgins et al. |
| 2006/0057223 A1 | 3/2006 | Dimauro et al. |
| 2006/0057693 A1 | 3/2006 | Simon |
| 2006/0121002 A1 | 6/2006 | Rolland et al. |
| 2006/0171948 A1 | 8/2006 | Weinstein et al. |
| 2006/0175244 A1 | 8/2006 | Dorian et al. |
| 2006/0175268 A1 | 8/2006 | Dorian et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0075016 A1 | 4/2007 | Leach |
| 2007/0092494 A1 | 4/2007 | Higgins et al. |
| 2007/0093834 A1 | 4/2007 | Stevens et al. |
| 2007/0207161 A1 | 9/2007 | Ralph |
| 2008/0011684 A1 | 1/2008 | Dorian et al. |
| 2008/0019964 A1 | 1/2008 | Olmarker et al. |
| 2008/0064626 A1 | 3/2008 | Zanella |
| 2008/0109018 A1 | 5/2008 | Martin |
| 2008/0161808 A1 | 7/2008 | Fox |
| 2008/0167668 A1 | 7/2008 | Criscuolo et al. |
| 2008/0193424 A1 | 8/2008 | Mckale et al. |
| 2008/0217263 A1 | 9/2008 | Higgins et al. |
| 2008/0268064 A1 | 10/2008 | Woodell-May |
| 2008/0269762 A1 | 10/2008 | Simon et al. |
| 2008/0294195 A1 | 11/2008 | Egli et al. |
| 2008/0306431 A1 | 12/2008 | Yoo |
| 2009/0014391 A1 | 1/2009 | Leach et al. |
| 2009/0047242 A1 | 2/2009 | Reinecke et al. |
| 2009/0101599 A1 | 4/2009 | Dorian et al. |
| 2009/0105767 A1 | 4/2009 | Reiley |
| 2009/0112146 A1 | 4/2009 | Wratten et al. |
| 2009/0171394 A1 | 7/2009 | Abdou |
| 2009/0181019 A1 | 7/2009 | Solinger |
| 2009/0191217 A1 | 7/2009 | De Wildt et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0198130 A1 | 8/2010 | Swift et al. |
| 2010/0226909 A1 | 9/2010 | Hecker et al. |
| 2010/0256595 A1 | 10/2010 | Leach et al. |
| 2011/0052561 A1 | 3/2011 | Hoeppner |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0093018 A1 | 4/2011 | Prasad et al. |
| 2011/0118796 A1 | 5/2011 | Reiley et al. |
| 2011/0129441 A1 | 6/2011 | Lentz |
| 2011/0189172 A1 | 8/2011 | Solinger et al. |
| 2011/0192804 A1 | 8/2011 | Landrigan et al. |
| 2011/0268708 A1 | 11/2011 | Lin et al. |
| 2012/0027746 A1 | 2/2012 | Dorian et al. |
| 2012/0093936 A1 | 4/2012 | Lindenberg et al. |
| 2012/0150086 A1 | 6/2012 | Cohen |

(56) References Cited

U.S. PATENT DOCUMENTS

| | | |
|---|---|---|
| 2012/0172836 A1 | 7/2012 | Higgins et al. |
| 2013/0178425 A1 | 7/2013 | Higgins et al. |
| 2013/0259951 A1 | 10/2013 | O'Connell, Jr. |
| 2013/0325076 A1 | 12/2013 | Palmer et al. |
| 2014/0018812 A1 | 1/2014 | Graham |
| 2014/0194999 A1 | 7/2014 | Orbay et al. |
| 2014/0358235 A1 | 12/2014 | Fox et al. |
| 2015/0088136 A1 | 3/2015 | Kotuljac et al. |
| 2016/0015437 A1 | 1/2016 | Elleby et al. |
| 2016/0270923 A1 | 9/2016 | Finley et al. |

FOREIGN PATENT DOCUMENTS

| | | |
|---|---|---|
| CN | 102048594 A | 5/2011 |
| CN | 102202611 A | 9/2011 |
| CN | 103767781 A | 5/2014 |
| CN | 105338990 A | 2/2016 |
| CN | 107072787 | 8/2017 |
| CN | 107548296 A | 1/2018 |
| DE | 102008010476 A1 | 8/2009 |
| EP | 0417818 A1 | 3/1991 |
| EP | 1813825 A1 | 8/2007 |
| EP | 2186877 A2 | 5/2010 |
| FR | 2844445 A1 | 3/2004 |
| JP | 2011512894 | 4/2011 |
| JP | 2012506264 | 3/2012 |
| JP | 2013542775 | 11/2013 |
| JP | 2018509987 A | 4/2018 |
| WO | WO-9905989 A2 | 2/1999 |
| WO | WO-9967277 A1 | 12/1999 |
| WO | WO-03063799 A2 | 8/2003 |
| WO | WO-03080104 A2 | 10/2003 |
| WO | WO-03088905 A2 | 10/2003 |
| WO | WO-2004009207 A1 | 1/2004 |
| WO | WO-2006043972 A1 | 4/2006 |
| WO | WO-2007121538 A1 | 11/2007 |
| WO | WO-2007128973 A2 | 11/2007 |
| WO | WO-2008021237 A1 | 2/2008 |
| WO | WO-2011031553 A3 | 3/2011 |
| WO | WO-2012030593 A2 | 3/2012 |
| WO | WO-2012030593 A3 | 3/2012 |
| WO | WO-2014149301 A1 | 9/2014 |
| WO | WO-2016160372 A2 | 10/2016 |
| WO | WO-2016160372 A3 | 10/2016 |

OTHER PUBLICATIONS

"European Application Serial No. 16741166.9, Response filed Jun. 20, 2018 to Office Action dated Dec. 20, 2017", 11 pgs.

"Australian Application Serial No. 2016243847, First Examination Report dated Sep. 11, 2019", 6 pgs.

"U.S. Appl. No. 14/661,250, Final Office Action dated Mar. 8, 2017", 11 pgs.

"U.S. Appl. No. 14/661,250, Non Final Office Action dated Sep. 1, 2016", 10 pgs.

"U.S. Appl. No. 14/661,250, Notice of Allowance dated May 17, 2017", 7 pgs.

"U.S. Appl. No. 14/661,250, Response filed May 8, 2017 to Final Office Action dated Mar. 8, 2017", 10 pgs.

"U.S. Appl. No. 14/661,250, Response filed Jul. 26, 2016 to Restriction Requirement dated May 27, 2016", 8 pgs.

"U.S. Appl. No. 14/661,250, Response filed Dec. 1, 2016 to Non Final Office Action dated Sep. 1, 2016", 12 pgs.

"U.S. Appl. No. 14/661,250, Restriction Requirement dated May 27, 2016", 9 pgs.

"Bio-Rad Laboratories. Bio-Gel P Polyacrylamide Gel Instruction Manual", [Online]. Retrieved from the Internet: <www.bio-rad.com/webmaster/pdfs/9154 Bio-Gel P.pdf>, (Jun. 20, 2012), 14 pgs.

"GPS® II Platelet Concentrate System: The New Gold Standard", Product Brochure, (Sep. 2006), 14 pgs.

"GPS® II System, Gravitational Platelet Separation System", User Manual-Cell Factor Technologies, Inc., [Online]. Retrieved from the Internet: <http://www.cellfactortech.com/global _products.cfm,>, (Sep. 16, 2005), 13 pgs.

"GPS® II System, Gravitational Platelet Separation System, Accelerating the Body's Natural Healing Process", Cell Factor Technologies, Inc., [Online] retrieved form the internet: <http://www.cellfactortech.com/global_products.cfm>, printed Sep. 16, 2005, (2005), 16 pgs.

"GPS® III Platelet Separation System, Leadership through Technology", Biomet Biologics, Inc, (Jul. 2007), 8 pgs.

"GPS® Platelet Concentrate System", Cell Factor Technologies, Inc Biomet Orthopaedics, Inc., (Feb. 29, 2004), 9 pgs.

"International Application Serial No. PCT/US2014/016900, International Preliminary Report on Patentability dated Sep. 24, 2015", 9 pgs.

"International Application Serial No. PCT/US2014/016900, International Search Report dated May 12, 2014", 5 pgs.

"International Application Serial No. PCT/US2014/016900, Written Opinion dated May 12, 2014", 8 pgs.

"International Application Serial No. PCT/US2016/023094, International Search Report dated Nov. 3, 2016", 7 pgs.

"International Application Serial No. PCT/US2016/023094, Invitation to Pay Add'l Fees and Partial Search Report dated Aug. 31, 2012", 7 pgs.

"International Application Serial No. PCT/US2016/023094, Written Opinion dated Nov. 3, 2016", 9 pgs.

"Isolation of Granulocytes From Human Peripheral Blood by Density Gradient Centrifugation", Miltenyi Biotec GmbH, (2008), 2 pgs.

"Plasmax Plasma Concentrate", Biomet Biologics, Inc, Brochure, (2006), 6 pgs.

"Plasmax® Plasma Concentration System", Biomet Biologics, (Mar. 2007), 18 pgs.

"Shoulder Recovery with the GPS® Platelet Concentrate System, Rotator Cuff Surgical Techniques", Biomet Biologics, Inc., (2004), 6 pgs.

"Update for veterinarians", Anonymous, [Online]. Retrieved from the Internet: <URL:http://vet.osu.edu/sites/default/files/documents/pdf/news/vmc/ovmaVeterinarianUp/documents/pdf /news/vmc/ovmaVeterinarianUp>, (Dec. 2012).

"Vortech Concentration System Product", Biomet Biologics, Inc., (Aug. 2005), 16 pgs.

Alford, J Winslow, et al., "Cartilage Restoration, Part 1. Basic Science, Historical Perspective, Patient Evaluation, and Treatment Options", The American Journal of Sports Medicine, 33(2), (2005), 295-306.

Anitua, Eduardo, et al., "Autologous platelets as a source of proteins for healing and tissue regeneration", Thromb Haemost, vol. 91, (2004), 4-15.

Arend, W, et al., "Interleukin-1 Receptor Antagonist: Role in Biology", Annu. Rev. Immunol., vol. 16, (1998), 27-55.

Baltzer, A W, et al., "Autologous conditioned serum (Orthokine) is an effective treatment for knee osteoarthritis. Osteoarthritis Cartilage", (Feb. 1, 2009), 152-60.

Becker, C, et al., "Efficacy of epidural perineural injections with autologous conditioned serum for lumbar radicular compression an Investigator-initiated, prospective, double-blind, reference-controlled study", (2007), 1803-1808.

Bendele, Alison M, et al., "Combination Benefit of Treatment With the Cytoki Ne Inhibitors interleukin-1 Receptor Antagonist and Pegylated Soluble Tumor Necrosis Factor Receptor Type I in animal models of Rheumatoid Arthritis", Arthritis & Rheumatism, Wiley, US, vol. 43, No. 1, (Dec. 1, 2000), 2648-2659.

Bielecki, T, et al., "Antibacterial effect of autologous platelet gel enriched with growth factors and toher acive substances", J Bone Joint Surg, vol. 89-B, No. 3, (Mar. 2007), 417-420.

Burnouf, T, "Blood-derived, tissue engineering biomaterials", Biomedical Engineering-Applications, Basis & Communications, val, 16, No. 6, (Dec. 6, 2004), 294-304.

Carpenter, et al., "Long-term storage of proteins", Current Protocols in Protein Science, (2002), 6 pgs.

(56) References Cited

OTHER PUBLICATIONS

Carpenter, et al., "Rationale Design of stable protein formulations—theory and practice", Rationale design of stable lyophilized protein formulations: theory and practice (2002), 109-133.
Dallari, et al., "Enhanced Tibial Osteotomy Healing with Use of Bone Grafts Supplemented with Platelet Gel or Platelet Gel and Bone Marrow Stromal Cells", The Journal of Bone and Joint Surgery, vol. 89, (2007), 2413-2420.
Dinarello, C, "Interleukin-1 and Interleukin-1 Antagonism", Blood, vol. 77, No. 8, (Apr. 1991), 1627-1652.
Dinarello, C A, "Interleukin-1 in the pathogenesis and treatment of inflammatory diseases", Blood, 2011, vol. 117(14),, (2011), 3720-3732.
Eppley, et al., "Platelet Quantification and Growth Factor Analysis from Platelet-Rich Plasma: Implications for Wound Healing", Plastic and Reconstructive Surgery, 114(6), (Nov. 2004), 1502-1508.
Evans, C H, "Novel biological approaches to the intra-articular treatment of osteoarthritis", BioDrugs, (2005), 355-62.
Fiotti, et al., "Atherosclerosis and Inflammation. Patterns of Cytokine Regulation in Patients with Peripheral Arterial Disease", Atherosclerosis. Elsevier Ireland Ltd. IE, vol. 145, No. 1, (Jul. 1, 1999), 51-60.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.
Hou, W H, et al., "Microfluidic Devices for Blood Fractionation", Micromachines, (2011), 319-343.
Juge-Aubry, C, et al., "Adipose Tissue is a Major Source of Interleukin-1 Receptor Antagonist: Upregulation in Obesity and Inflammation", Diabetes, vol. 52, (May 2004), 1104-1110.
Kaufman, A, et al., "Human macrophage response to UHMWPE, TiAIV, Coer, and alumina particles: Analysis of multiple cytokines using protein arrays", Journal of Biomedical Materials Research Part A, published online in Wiley InterScience, (Jul. 2007), 464-474.
Kim, Seon Hee, et al., "Ex Vivo Gene Delivery of Il-Lra and Soluble Tnf Receptor Confers a Distal Synergistic Therapeutic Effect in Antigen-Induced Arthritis", Molecular Therapy, Nature Publishing Group, GB, vol. 6, No. 5, (Nov. 1, 2002), 591-600.
King, William, et al., "A Simple Method to Correlate the Concentration of an Anti-Inflammatory Cytokine with White Blood Cells in an Autologous Protein Solution", [Online]. Retrieved from the Internet: <URL:http://prgmobileapps.com/AppUpdates/ors/Abstracts/abs391.html>, (Feb. 24, 2014).
Klingenberg et al., "Treating inflammation in Atherosclerotic Cardiovascular Disease: Emerging Therapies", European Heart Journal., vol. 30, No. 23, (Dec. 2009), 2838-2844.
Lavi, Galia, et al., "Sustained delivery of IL-1 Ra from biodegradable microspheres reduces the No. Of murine 816 melanoma lung metastases", Journal of Controlled Release, 123, (2007), 123-130.
Lucarelli, E, et al., "Platelet-derived growth factors enhance proliferation of human stromal stem cells", Biomaterials, vol. 24, (2003), 3095-3100.
Matthews, J, et al., "Comparison of the response of primary human peripheral blood mononuclear phagocytes from different donors to challenge with model polyethylene particles of known size and dose", Biomaterials, vol. 21, (2000), 2033-2044.
Meijer, H, et al., "The production of antiinflammatory cytokines in whole blood by physico-chemical induction", Inftamm. Res. vol. 52, (Oct. 2003), 404-407.
Morizaki, et al., "The Effects of Platelet-Rich Plasma on Bone Marrow Stromal Cell Transplants for Tendon Healing in Vitro", J. Hand Surg. Am., vol. 35, No. 11, (Nov. 2010), 1833-1841.
Murphy, Michael P, et al., "Autologous Bone Marrow Mononuclear Cell Therapy is Safe and Promotes Amputation-Free Survival in Patients With Critical Limb Ischemia", Journal of Vascular Surgery, C.V. Mosby CO., St. Louis, MO, US, vol. 53, No. 6, (Jan. 28, 2011), 1565-1574.
Muzio, M, et al., "Interleukin-13 Induces the Production of Interleukin-1 Receptor Antagonist (IL-1ra) and the Expression of the mRNA for the Intracellular (Keratinocyte) Form of IL-1ra in Human Myelomonocylic Cells", Blood, vol. 83, No. 7, (Apr. 1994), 1738-1743.
Nursen, Duzgun, et al., "Cytokine inhibitors: soluble tumor necrosis factor receptor 1 and interleukin-1 receptor antagonist in Behcet's disease", Rheumatology International ; Clinical and Experimental Investigations, Springer, Berlin, DEvol. 25, No. 1, (Jan. 2005), 1-5.
O'Shaughnessey, Krista M, et al., "Blood-derived antiinflammatory protein solution blocks the effect of IL-1 beta on human macrophages in vitro", Imflammation Research, vol. 60, No. 10,, (Oct. 1, 2011), 929-936.
Rader, C, et al., "Cytokine Response of Human Macrophage-like Cells After Contact With Polyethylene and Pure Titanium Particles", The Journal of Arthroplasty, vol. 14, No. 7, (Oct. 1999), 840-848.
Sorbera, L A, "Pegsunercept. Pegylated Soluble Tumor Necrosis Factor Receptor Type 1 Peg-Stnf-RI", Drugs of the Future, Prous Science, ES, vol. 28, No. 12, (Jan. 1, 2003), 1182-1188.
Swift, Matthew J, "Characterization of Growlh Factors in Platelet Rich Plasma", Cell Factor Technologies, Inc, [Online]. Retrieved from the Internet: www.cellfactortech.com/global_products.cfm, (Sep. 16, 2005), 1 pg.
Tateishi-Yuyama, E, et al., "Therapuetic angiogenesis for patients with limb ischaemia by autologous transplantation of bone-barrow cells: a pilot study and randomised controlled trial", The Lancet, (2002), 427-435.
Ulich, Thomas R, et al., "Intratrachael Administration of Endotoxin and Cytokines: IV. The Soluble Tumor Necrosis Factor Receptor Type 1 Inhibits Acute Inflammation", American Journal of Pathology; vol. 142, No. 5, (May 1993).
Vangsness, Thomas, et al., "Stimulation of IL-1ra production from platelet-rich plasma", Poster No. 488 presented at 54th Annual Meeting of the Orthopedic Research Society, Mar. 2-5, 2008), 1 pg.
Woodell-May, J, et al., "Effect of Incubation Time on Production of IL-1ra and sTNF-RI from Platelet-Rich Plasma", Paper No. 200, 55th Annual Meeting of the Orthopaedic Research Society, (Feb. 2009).
Woodell-May, J, et al., "Elution of IL-1ra from a concentrated-plasma matrix—An in vitro study", Poster Presentation at 8th World Congress of the International Cartilage Repair Society, (May 2009), 1 pg.
Woodell-May, J, et al., "Producing Accurate Platelet Counts for Platelet Rich Plasma: Validation of a Hematology Analyzer and Preparation Techniques for Counting", Scientific Foundation. Journal of Carniofacial Surgery, vol. 16, No. 5, (Sep. 2005), 749-756.
Woodell-May, Jennifer, et al., "Autologous Protein Solution Inhibits Mmp-13 Production by Il-L[Beta] and Tnf[Alpha]-Stimulated Human Articular Chondrocytes", Journal of Orthopaedic Research, vol. 29, No. 9, (Sep. 1, 2011), 1320-1326.
Wright-Carpenter, T, "Treatment of Muscle Injuries by Local Administration of Autologous Conditioned Serum: A Pilot Study on Sportsmen with Muscle Strains", Int J Sports Med, vol. 25, (Oct. 2004), 588-593.
Yang, et al., "Protective effects of IL-1Ra or vIL-10 gene transfer on a murine model of wear debris-included osteolysis", Gene Therapy 11, (2004), 483-491.
Yang, T, et al., "Recent Applications of Polyacrylamide as Biomaterials", Recent Patents on Materials Science, vol. 1, (2008), 29-40.
Yoshida, S, et al., "Elevation of serum soluble tumour necrosis factor (TNF) receptor and IL-1 receptor antagonist levels in bronchial asthma", Clinical and Experimental Immunology, Wiley-Blackwell Publishing Ltd. vol. 106, No. 1, (Oct. 1, 1996), 73-78.
Zhang, et al., "IL-1ra alleviates inflammatory hyperalgesia through preventing phosphorylation of NMDA receptor NR-1 subunit in rats", Pain, vol. 135, No. 3, (Mar. 5, 2008), 232-239.
"Australian Application Serial No. 2016243847, Response filed Nov. 13, 2019 to First Examination Report dated Sep. 11, 2019", 23 pgs.
"Australian Application Serial No. 2016243847, Subsequent Examiners Report dated Dec. 5, 2019", 3 pgs.

(56) References Cited

OTHER PUBLICATIONS

"Chinese Application Serial No. 201680023978.7, Office Action dated Sep. 4, 2019", W/English Translation, 16 pgs.

"Chinese Application Serial No. 201680023978.7, Response filed Dec. 10, 2019 to Office Action dated Sep. 4, 2019", w/ English Claims, 9 pgs.

"Japanese Application Serial No. 2017-549201, Notification of Reasons for Refusal dated Jan. 21, 2020", with English translation, 11 pages.

"Australian Application Serial No. 2016243847, Response filed Feb. 25, 2020 Subsequent Examiners Report dated Dec. 5, 2019", 22 pages.

"Chinese Application Serial No. 201680023978.7, Office Action dated Mar. 11, 2020", with English translation, 16 pages.

"European Application Serial No. 16741166.9, Communication Pursuant to Article 94(3) EPC dated Apr. 1, 2020", 4 pages.

IMPLANT CONFIGURED FOR HAMMERTOE AND SMALL BONE FIXATION

FIELD

The present disclosure relates generally to bone fixation systems and, more particularly, to fixation devices and techniques for bone fusion to correct a hammertoe condition.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Deformities of the fingers and toes are common conditions encountered by orthopedists and podiatrists. Patients with digital deformities often experience significant pain from structural abnormalities. Some of these abnormalities are acquired, caused by traumatic injuries, neuromuscular pathologies, systemic diseases, or mechanical problems secondary to extrinsic pressures. The deformities are popularly known as either mallet finger, jersey finger, coach's finger, hammer toe, as well as a host of others indicative of several different pathologies.

Hammer toe is generally described in medical literature as an acquired disorder, typically characterized by hypertension of the metatarsophalangeal joint (MTPJ), hyperflexion of the proximal interphalangeal joint (PIPJ), and hypertension of the distal interphalangeal joint (DIPJ). Although this condition can be conservatively managed such as through the use of orthotic devices, in certain instances surgical intervention is required.

To ensure success of a surgical procedure, a proximal interphalangeal (PIP) joint arthrodesis is typically performed. Newer implants sued in hammertoe procedures fuse only the hammertoe joint but require the surgeon to distract the DIPJ in order to extend over the distal end of the implant after the first half of the implant has been inserted into PIPJ. It can be difficult to perform such steps in a minimally invasive fashion. In this regard, the distraction can cause issues with nerves and blood supply to the distal end of the toe.

SUMMARY

This section provides a general summary of the disclosure, and is not a comprehensive disclosure of its full scope or all of its features.

An implant configured for fusing a first bone segment and a second bone segment during an operative procedure and constructed in accordance to one example of the present disclosure includes an implant body, a first bone interfacing portion and a second bone interfacing portion. The implant body can extend longitudinally between an insertion end and an opposite end. The first bone interfacing portion can be provided on the implant body and be configured to be implanted relative to the first bone segment. The second bone interfacing portion can be provided on the implant body and be configured to be implanted relative to the second bone segment. The first and second bone interfacing portions can be inserted dorsally into the first and second bone segments, respectively.

According to additional features, the first bone interfacing portion can further comprise a first insertion portion that generally tapers toward the insertion end. The first insertion portion can be conical. The second bone interfacing portion can further comprise a second insertion portion that generally tapers toward the insertion end. The second bone interfacing portion can be conical.

According to other features, the first bone interfacing portion can further comprise first and second engagement portions formed at the opposite end. The first insertion and engagement portions can be offset by a first connecting shaft. The second insertion and engagement portions can be offset by a second connecting shaft. The first engaging portion can extend along a first bone engaging axis. The second bone engaging portion can extend along a second bone engaging axis. In one configuration, the first and second axes can be parallel. In another configuration, the first and second axes can converge toward the insertion end. In another configuration, the first and second axes can diverge toward the insertion end.

According to still other features, the implant can further comprise a porous metal portion disposed between (i) the first insertion portion and the first engagement portion and (ii) the second insertion portion and the second engagement portion. The implant body can further comprise a wedge disposed between the first and second bone interfacing portions. The wedge can generally extend between and taper from the opposite end to the insertion end. The wedge can include (i) a first bone engaging face configured to engage the first bone segment and (ii) a second engaging face configured to engage the second bone segment. The first and second bone engaging faces can extend along converging planes. The first and second engagement portions can comprise a geometry that defines two intersecting circles.

An implant configured for fusing a first bone segment and a second adjacent bone segment during an operative procedure according to another example of the present disclosure includes an implant body, a first bone interfacing portion, a second bone interfacing portion and a wedge. The implant body can have a solid metal portion and a porous metal portion. The implant body can extend longitudinally between an insertion end and an opposite end. The first bone interfacing portion can be provided on the implant body and have a first tapered end. The first bone interfacing portion can be configured to be implanted relative to the first bone segment. The second bone interfacing portion can be provided on the implant body and have a second tapered end. The second bone interfacing portion can be configured to be implanted relative to the second bone segment. The wedge can be configured on the implant body between the first and second bone interfacing portions. The wedge can generally extend between and taper from the opposite end to the insertion end. The first and second bone interfacing portions can be inserted dorsally into the first and second bone segments, respectively.

According to other features, the wedge can include (i) a first bone engaging face configured to engage the first bone segment and (ii) a second bone engaging face configured to engage the second bone segment. The first and second bone engaging faces can extend along converging planes. The first and second engagement portions comprise a geometry that defines two intersecting circles. The first and second engagement portions can extend along longitudinal axes that converge. In another example, the first and second engagement portions can extend along longitudinal axes that diverge.

A method of inserting an implant into a first bone segment and a second adjacent bone segment to fuse the first bone segment to the second bone segment is provided. An implant body is provided having a first and a second bone interfacing portion that extend longitudinally between an insertion end and an opposite end. A first bone hole is prepared generally inferiorly into the first bone segment. A second bone hole is prepared generally inferiorly into the second bone segment. The first and second bone interfacing portions are inserted dorsally into the respective first and second bone holes thereby fusing the first and second bone segments together.

According to additional features of the method, a first conically shaped insertion portion formed on the first bone interfacing portion is located into the first bone hole. A second conically shaped insertion portion formed on the second bone interfacing portion is located into the second bone hole. The first and second bone interfacing portions are concurrently advanced into the respective first and second bone holes. The implant can further comprise a wedge generally extending between the first and second bone interfacing portions. The wedge can include (i) a first bone engaging face configured to engage the first bone segment and (ii) a second bone engaging face configured to engage the second bone segment. The first and second bone engaging faces can extend along converging planes. The first bone engaging face can be slidably advanced along the first bone segment concurrently to the second bone engaging face slidably advancing along the second bone segment.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

DETAILED DESCRIPTION

The following description is merely exemplary in nature and is not intended to limit the present disclosure, its application, or uses. Examples are provided so that this disclosure will be thorough, and will fully convey the scope to those who are skilled in the art. Numerous specific details are set forth such as examples of specific components, devices, systems and/or methods, to provide a thorough understanding of the present disclosure. It will be apparent to those skilled in the art that specific details need not be employed, that examples shown herein may be embodied in many different forms and that neither should be construed to limit the scope of the disclosure.

The present teachings and related discussion is directed primarily to the treatment of a hammertoe condition, it is equally applicable to any situation where a first phalange and a second adjacent phalange, of either a toe or a finger, are to be joined or fused together. It will further be appreciated that while the following discussion is directed toward treatment of a hammertoe condition, the following implants may be additionally used in other bones. In this regard, the following disclosure is not limited to implants used in phalanges. In other examples, the following implants may be used on any adjacent bones or on a fractured bone. As used herein the term "bone segment" is used to refer to a bone or a bone portion resulting from a fracture.

Figures 1, 2, 3:
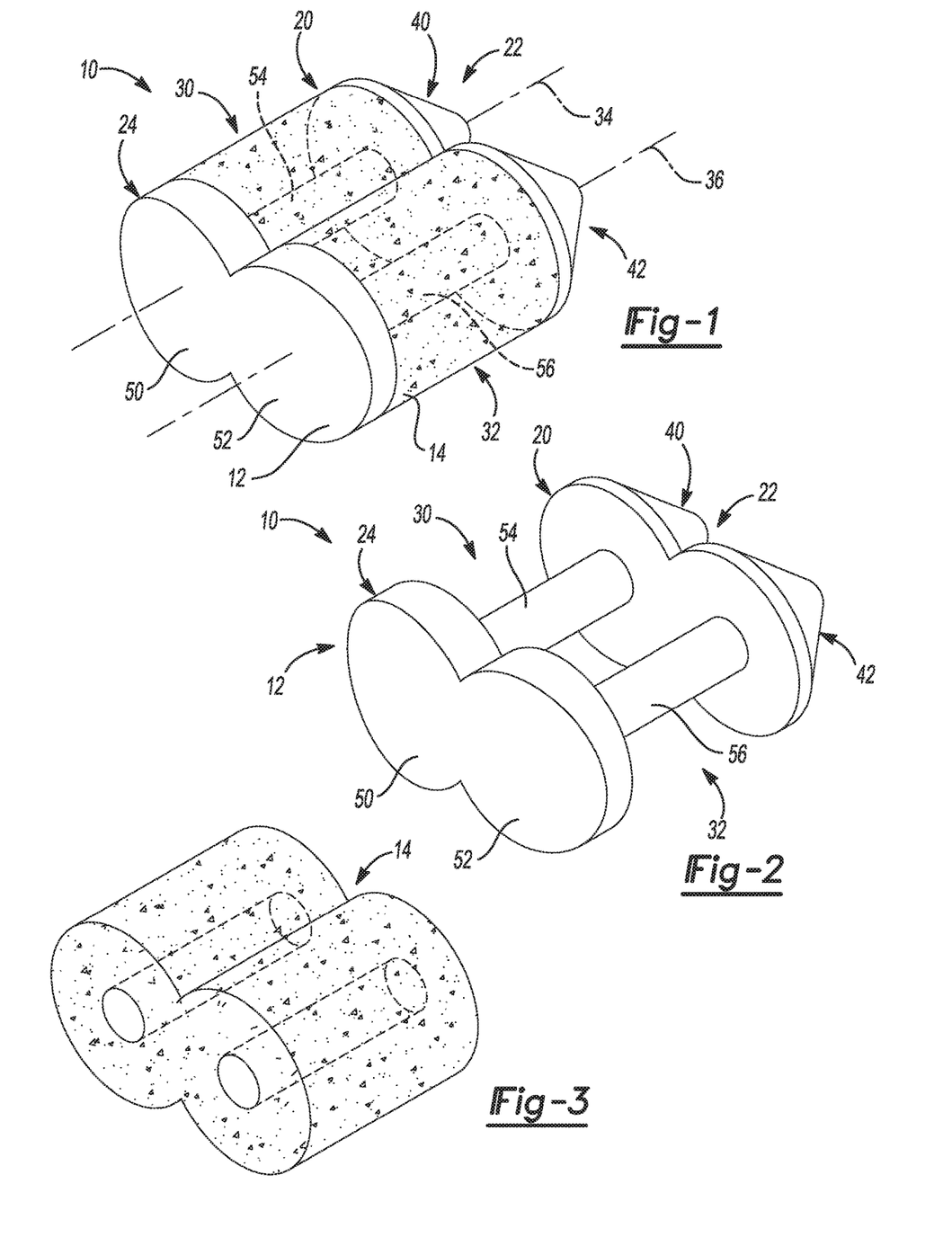
FIG. 1 is a perspective view of an implant configured for fusing a first phalange and a second adjacent phalange and constructed in accordance to one example of the present disclosure.
FIG. 2 is a perspective view of a solid metal portion of the implant of FIG. 1.
FIG. 3 is a perspective view of a porous metal portion of the implant of FIG. 1.

With initial reference to FIGS. 1-3, an exemplary implant configured for fusing a first phalange and a second adjacent phalange during an operative procedure is shown and generally identified at reference numeral 10. The implant 10 can be formed of a biocompatible alloy, such as a titanium alloy. In one exemplary implementation, the implant 10 can be formed using an additive manufacturing process with a titanium alloy core 12 (FIG. 2) and a porous metal titanium alloy structure 14 (FIG. 3).

In one exemplary implementation, the porous metal structure 14 can be a formed from a titanium alloy using an additive Manufacturing process, such as with OsseoTi™, which is commercially available from Biomet Manufacturing, LLC (Warsaw, Ind., USA). Briefly, however, OsseoTi™ is highly biocompatible, has high corrosion resistance and includes a highly interconnected porous architecture that mimics the porous structure cancellous bone, which can enhance bone integration and in-growth. In one exemplary implementation, OsseoTi™ can include a porous construct with a porosity of 70%.

The implant 10 includes an implant body 20 that extends longitudinally between an insertion end 22 and an opposite end 24. The implant body 20 further includes a first bone interfacing portion 30 and a second bone interfacing portion 32. The first bone interfacing portion 30 extends along a first bone engaging axis 34 and is configured to be implanted relative to a first phalange. The second bone interfacing portion 32 extends along a second bone engaging axis 36 and is configured to be implanted relative to a second phalange. In the example shown in FIGS. 1-3, the first and second axes 34 and 36 are parallel to each other. As will be described herein, the first and second bone interfacing portions 30 and 32 are configured to be inserted dorsally along the respective first and second bone engaging axes 34 and 36 and into the first and second phalanges, respectively.

The first bone interfacing portion 30 can include a first insertion portion 40. The first insertion portion 40 can generally be in the geometry of a cone having a conical profile that tapers toward the insertion end 20. Similarly, the second bone interfacing portion 32 can include a second insertion portion 42. The second insertion portion 42 can generally be in the geometry of a cone having a conical profile that tapers toward the insertion end 20.

The first bone interfacing portion 30 further first engagement portion 50 formed at an opposite end of the first insertion portion 40. The second bone interfacing portion 32 further includes a second engagement portion 52 formed at an opposite end of the second insertion portion 42. The first engagement portion 50 and the first insertion portion 40 can be connected and offset relative to each other by a first connecting shaft 54. Similarly, the second engagement portion 52 and the second insertion portion 42 can be connected and offset relative to each other by a second connecting shaft 56. In one configuration, the first and second engagement portions 50 and 52 can provide a surface for engaging during advancing the implant 10 into the respective first and second phalanges. In the example shown, the first and second engagement portions 50 and 52 have a geometry that defines two intersecting circles. Other configurations are contemplated. As shown in FIGS. 1-3, the porous metal structure 14 is generally disposed on the core 12 between the first and second insertion portions 40, 42 and the first and second engagement portions 50, 52. In particular, the first and second insertion portions 40 and 42 can be formed of solid core 12 to assist in insertion of the implant 10 into the respective first and second phalanges.

Figures 4, 5, 6:
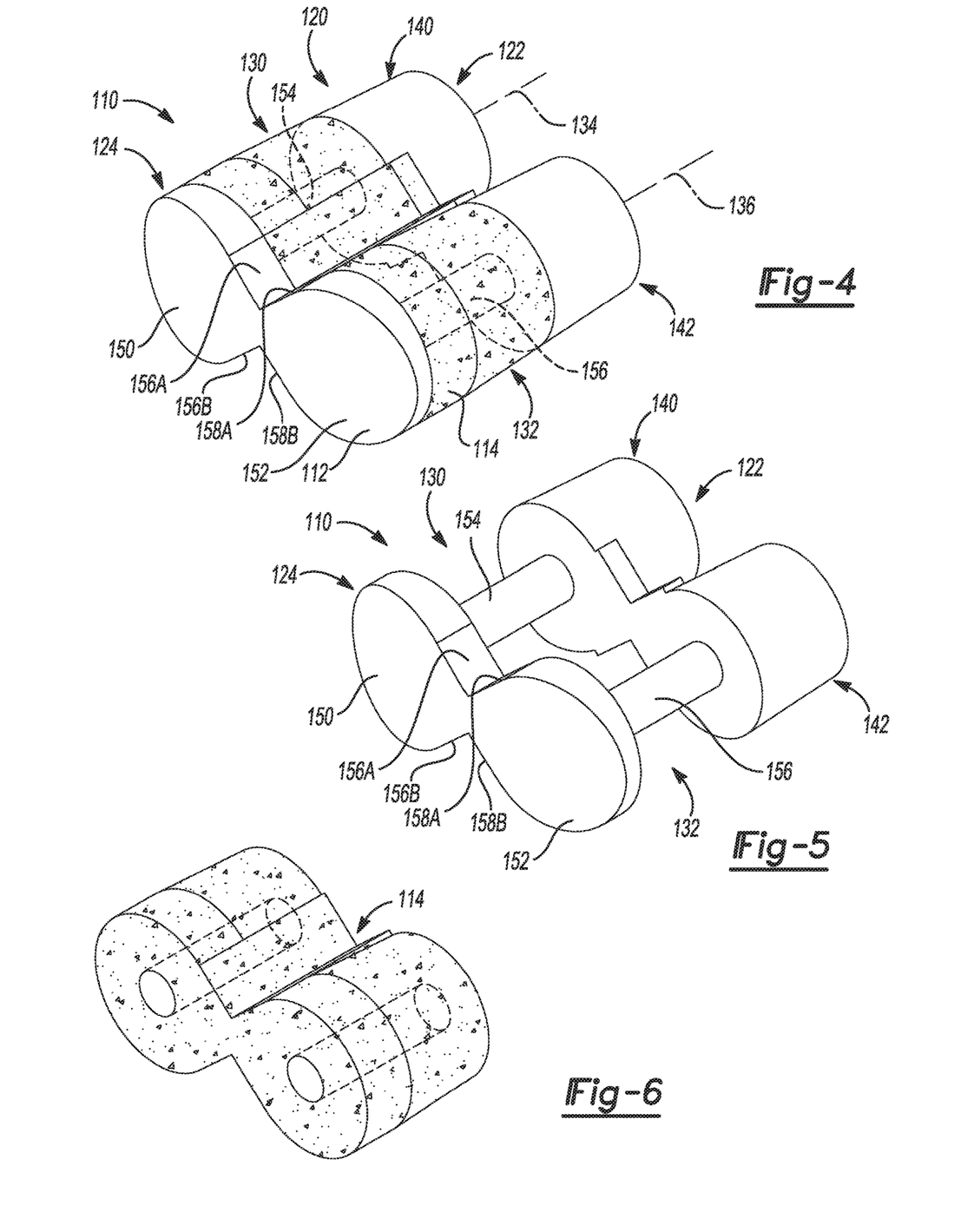
FIG. 4 is a perspective view of an implant configured for fusing a first phalange and a second adjacent phalange and constructed in accordance to another example of the present disclosure.
FIG. 5 is a perspective view of a solid metal portion of the implant of FIG. 4.
FIG. 6 is a perspective view of a porous metal portion of the implant of FIG. 4.

With reference now to FIGS. 4-6, an implant configured for fusing a first phalange and a second adjacent phalange during an operative procedure and constructed in accordance to another example is shown and generally identified at reference numeral 110. The implant 110 can be formed of a biocompatible alloy, such as a titanium alloy. The implant 110 can be formed using an additive manufacturing process identified above with a titanium core 112 (FIG. 5) and a porous metal titanium alloy structure 114 (FIG. 6). The porous metal alloy structure 114 may be formed of OsseoTi described above.

The implant 110 can include an implant body 120 that extends longitudinally between an insertion end 122 and an opposite end 124. The implant body 120 further includes a first bone interfacing portion 130 and a second bone interfacing portion 132. The first bone interfacing portion 130 extends along a first bone engaging axis 134 and is configured to be implanted relative to a first phalange. The second bone interfacing portion 132 extends along a second bone engaging axis 136 and is configured to be implanted relative to a second phalange. In the example shown in FIGS. 4-6, the first and second axes 134 and 136 are parallel to each other. As will be described herein, the first and second bone interfacing portions 130 and 132 are configured to be inserted dorsally, similar to the other examples disclosed herein, along the respective first and second bone engaging axes 134 and 136 and into the first and second phalanges, respectively.

The first bone interfacing portion 130 can include a first insertion portion 140. The first insertion portion 140 can taper toward the insertion end 120. In another example, the first insertion portion 140 can have a conical profile similar to shown in FIGS. 1-3. Similarly, the second bone interfacing portion 132 can include a second insertion portion 142. The second insertion portion 142 can also taper toward the insertion end 122 and/or have a conical profile similar to shown in FIGS. 1-3. Regardless, the outer surface of the first and second insertion portions 140 and 142 are to facilitate easy insertion into a prepared bone hole as will become appreciated herein.

The first bone interfacing portion 130 further includes a first engagement portion 150 formed at an opposite end of the first insertion portion 140. The second bone interfacing portion 132 further includes a second engagement portion 152 formed at an opposite end of the second insertion portion 142. The first engagement portion 150 and the first insertion portion 140 can be connected and offset relative to each other by a first connecting shaft 154.

Similarly, the second engagement portion 152 and the second insertion portion 142 can be connected and offset relative to each other by a second connecting shaft 156. In one configuration, the first and second engagement portions 150 and 152 can provide a surface for engaging during advancing the implant 110 into the respective first and second phalanges. In the example shown, the first and second engagement portions 150 and 152 have a geometry that generally defines two converging teardrops. In this regard, the engagement portion 150 has a first pair of generally planar surfaces 156A, 156B and the second engagement portion 152 has a second pair of generally planar surfaces 158A and 158B. The corresponding first and second planar surfaces 156A and 158A intersect and the first and second planar surface 156B and 158B intersect.

As will be explained in greater detail herein, the first and second pairs of planar surfaces 156A, 156B and 158A, 158B can correspond to cuts made in the respective adjacent phalanges to accommodate the implant 110. Other configurations are contemplated. As shown in FIGS. 4-6, the porous metal structure 114 is generally disposed on the core 112 between the first and second insertion portions 140, 142 and the first and second engagement portions 150, 152. In particular, the first and second insertion portions 140 and 142 can be formed of solid core 112 to assist in insertion of the implant 110 into the respective first and second phalanges.

Figures 7, 8, 9:
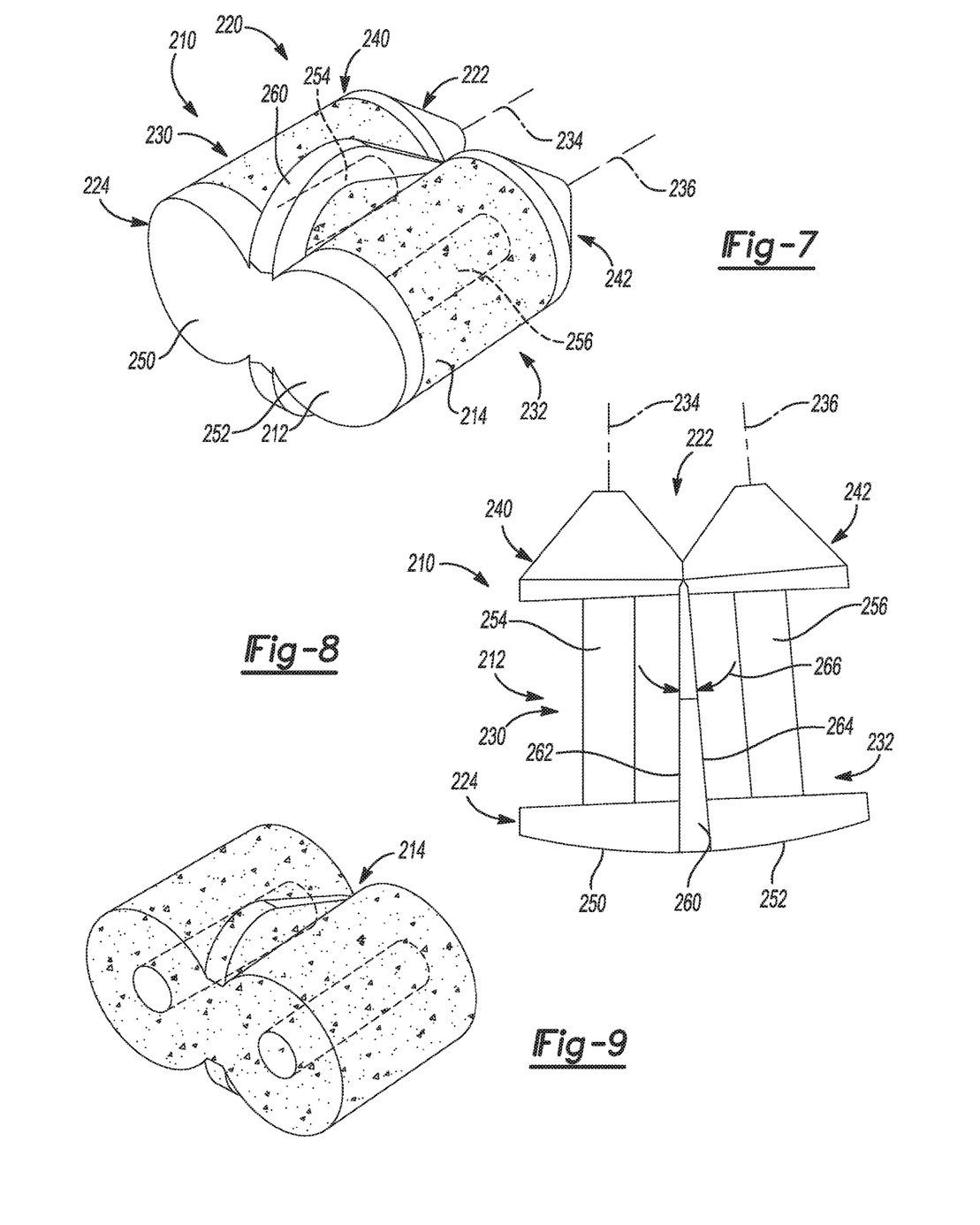
FIG. 7 is a perspective view of an implant configured for fusing a first phalange and a second adjacent phalange and constructed in accordance to yet another example of the present disclosure.
FIG. 8 is a perspective view of a solid metal portion of the implant of FIG. 7.
FIG. 9 is a perspective view of a porous metal portion of the implant of FIG. 7.

With reference now to FIGS. 7-9, an implant configured for fusing a first phalange and a second adjacent phalange during an operative procedure and constructed in accordance to another example is shown and generally identified at reference numeral 210. The implant 210 can be formed of a biocompatible alloy, such as a titanium alloy. The implant 210 can be formed using an additive manufacturing process identified above with a titanium core 212 (FIG. 8) and a porous metal titanium alloy structure 214 (FIG. 9). The porous metal alloy structure 214 may be formed of OsseoTi described above.

The implant 210 can include an implant body 220 that extends longitudinally between an insertion end 222 and an opposite end 224. The implant body 220 further includes a first bone interfacing portion 230 and a second bone interfacing portion 232. The first bone interfacing portion 230 extends along a first bone engaging axis 234 and is configured to be implanted relative to a first phalange. The second bone interfacing portion 232 extends along a second bone engaging axis 236 and is configured to be implanted relative to a second phalange. As best illustrated in FIG. 8, the first and second axes 234 and 236 define converging axes. As will be described herein, the first and second bone interfacing portions 230 and 232 are configured to be inserted dorsally, similar to the other examples disclosed herein, along the respective first and second bone engaging axes 234 and 236 and into the first and second phalanges, respectively.

The first bone interfacing portion 230 can include a first insertion portion 240. The first insertion portion 240 can taper toward the insertion end 222. In the example shown, first insertion portion 240 has a conical profile similar to shown in FIGS. 1-3. Similarly, the second bone interfacing portion 232 can include a second insertion portion 242. The second insertion portion 242 can also taper toward the insertion end 222 and/or have a conical profile similar to shown in FIGS. 1-3. Regardless, the outer surface of the first and second insertion portions 240 and 242 are configured to facilitate easy insertion into a prepared bone hole as will become appreciated herein.

The first bone interfacing portion 230 further includes a first engagement portion 250 formed at an opposite end of the first insertion portion 240. The second bone interfacing portion 232 further includes a second engagement portion 252 formed at an opposite end of the second insertion portion 242. In the example shown in FIG. 18, the first and second engagement portions 250 and 252 can collectively have an arcuate outer profile. The first engagement portion 250 and the first insertion portion 240 can be connected and offset relative to each other by a first connecting shaft 254.

Similarly, the second engagement portion 252 and the second insertion portion 242 can be connected and offset relative to each other by a second connecting shaft 256. In one configuration, the first and second engagement portions 250 and 252 can provide a surface for engaging during advancing the implant 210 into the respective first and second phalanges. In the example shown, the first and second engagement portions 250 and 252 have a geometry that defines two disk shaped portions that converge into a central wedge 260. The wedge 260 includes first and second generally planar surfaces 262 and 264 (FIG. 8) that converge toward the insertion end 222. In one non-limiting example, the first and second planar surfaces 262 and 264 define an angle 266 of about 10 degrees. It will be appreciated that other angles may be provided. Moreover, it is contemplated that a kit of implants may be offered having a variety of geometries including various wedges 260 that may be selected intraoperatively according to a given patient's needs.

As will be explained in greater detail herein, the first and second planar surfaces 262 and 264 are configured to slidably engage respective phalanges during insertion of the implant 210 to further encourage the phalanges to obtain a desired orientation. As shown in FIGS. 7-9, the porous metal structure 214 is generally disposed on the core 212 between the first and second insertion portions 240, 242 and the first and second engagement portions 250, 252. In particular, the first and second insertion portions 240 and 242 can be formed of solid core 212 to assist in insertion of the implant 210 into the respective first and second phalanges.

Figure 10:
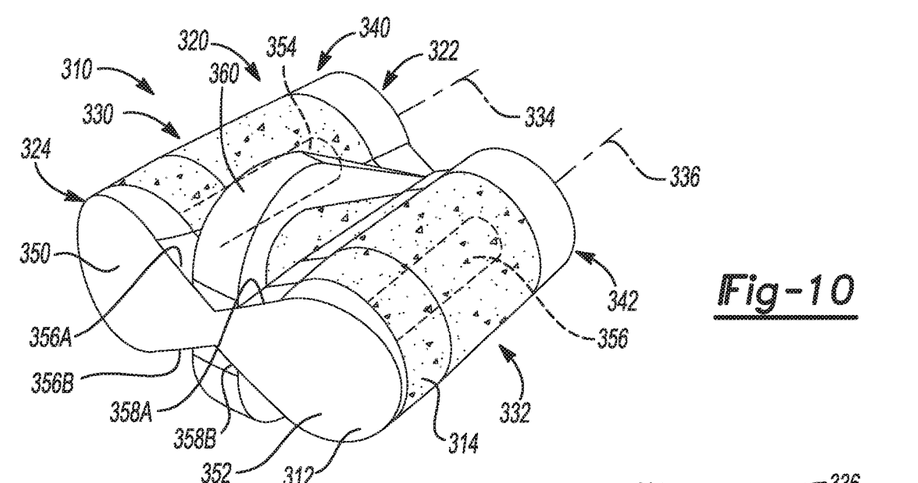
FIG. 10 is a perspective view of an implant configured for fusing a first phalange and a second adjacent phalange and constructed in accordance to another example of the present disclosure.
Figures 11, 12:
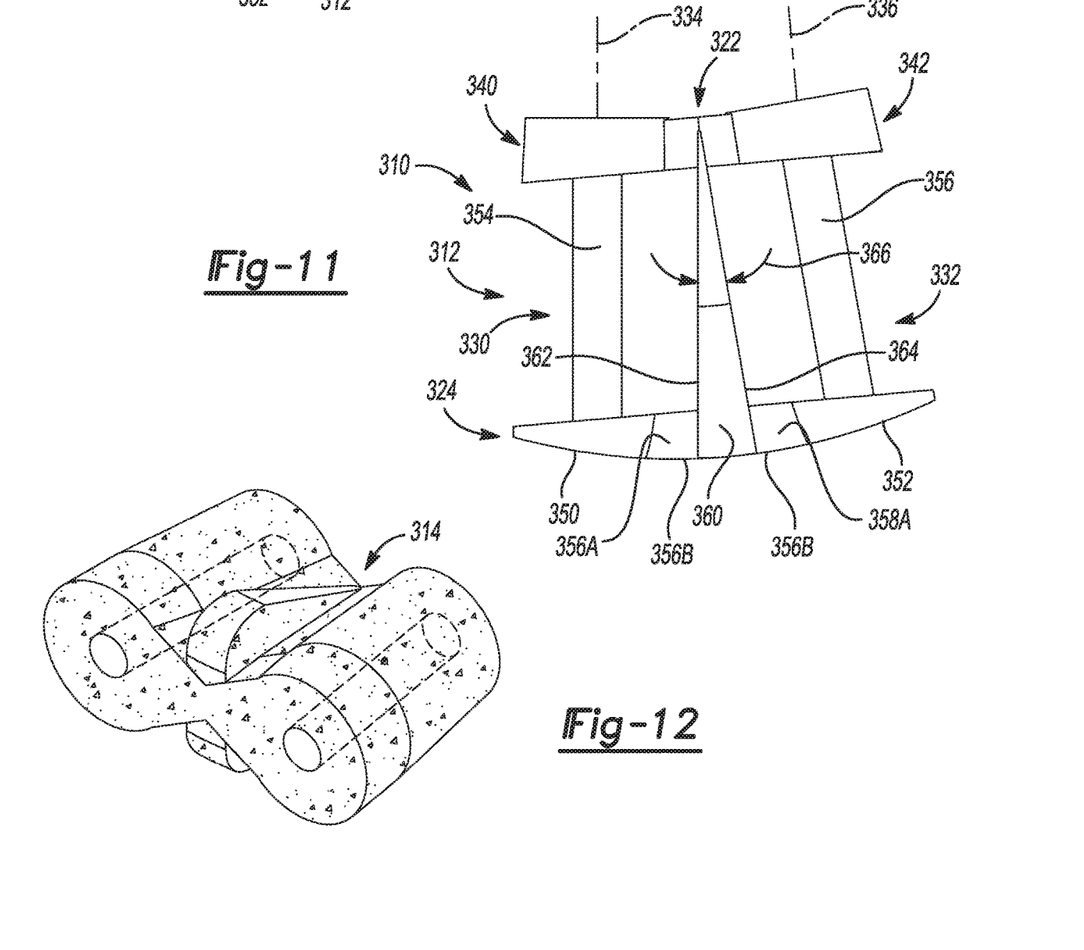
FIG. 11 is a perspective view of a solid metal portion of the implant of FIG. 10.
FIG. 12 is a perspective view of a porous metal portion of the implant of FIG. 10.

With reference now to FIGS. 10-12, an implant configured for fusing a first phalange and a second adjacent phalange during an operative procedure and constructed in accordance to another example is shown and generally identified at reference numeral 310. The implant 310 can be formed of a biocompatible alloy, such as a titanium alloy. The implant 310 can be formed using an additive manufacturing process identified above with a titanium core 312 (FIG. 11) and a porous metal titanium alloy structure 214 (FIG. 12). The porous metal alloy structure 314 may be formed of OsseoTi described above.

The implant 310 can include an implant body 320 that extends longitudinally between an insertion end 322 and an opposite end 324. The implant body 320 further includes a first bone interfacing portion 330 and a second bone interfacing portion 332. The first bone interfacing portion 330 extends along a first bone engaging axis 334 and is configured to be implanted relative to a first phalange. The second bone interfacing portion 332 extends along a second bone engaging axis 336 and is configured to be implanted relative to a second phalange. As best illustrated in FIG. 11, the first and second axes 334 and 336 define converging axes. As will be described herein, the first and second bone interfacing portions 330 and 332 are configured to be inserted dorsally, similar to the other examples disclosed herein, along the respective first and second bone engaging axes 334 and 336 and into the first and second phalanges, respectively.

The first bone interfacing portion 330 can include a first insertion portion 340. The first insertion portion 340 can taper toward the insertion end 322. In the example shown, first insertion portion 340 has a conical profile similar to shown in FIGS. 1-3. Similarly, the second bone interfacing portion 332 can include a second insertion portion 342. The second insertion portion 342 can also taper toward the insertion end 322 and/or have a conical profile similar to shown in FIGS. 1-3. Regardless, the outer surface of the first and second insertion portions 340 and 342 are configured to facilitate easy insertion into a prepared bone hole as will become appreciated herein.

The first bone interfacing portion 330 further includes a first engagement portion 350 formed at an opposite end of the first insertion portion 340. The second bone interfacing portion 332 further includes a second engagement portion 352 formed at an opposite end of the second insertion portion 342. In the example shown in FIG. 11, the first and second engagement portions 350 and 352 can collectively have an arcuate outer profile. The first engagement portion 350 and the first insertion portion 340 can be connected and offset relative to each other by a first connecting shaft 354.

Similarly, the second engagement portion 352 and the second insertion portion 342 can be connected and offset relative to each other by a second connecting shaft 356. In one configuration, the first and second engagement portions 350 and 352 can provide a surface for engaging during advancing the implant 310 into the respective first and second phalanges. In the example shown, the first and second engagement portions 350 and 352 have a geometry that defines two teardrops that converge into a central wedge 360. The first engagement portion 350 has a first pair of generally planar surfaces 356A, 356B and the second engagement portion 352 has a second pair of generally planar surfaces 358A and 358B. The corresponding first and second planar surfaces 356A and 358A intersect and the first and second planar surface 356B and 358B intersect.

The wedge 360 includes first and second generally planar surfaces 362 and 364 that converge toward the insertion end 322. In one non-limiting example, the first and second planar surfaces 362 and 364 define an angle 366 of about 10 degrees. It will be appreciated that other angles may be provided. Moreover, it is contemplated that a kit of implants may be offered having a variety of geometries including various wedges 360 that may be selected intraoperatively according to a given patient's needs.

As will be explained in greater detail herein, the first and second planar surfaces 362 and 364 are configured to slidably engage respective phalanges during insertion of the implant 310 to further encourage the phalanges to obtain a desired orientation. As shown in FIGS. 10-12, the porous metal structure 314 is generally disposed on the core 312 between the first and second insertion portions 340, 342 and the first and second engagement portions 350, 352. In particular, the first and second insertion portions 340 and 342 can be formed of solid core 312 to assist in insertion of the implant 310 into respective first and second phalanges.

Figure 13A:
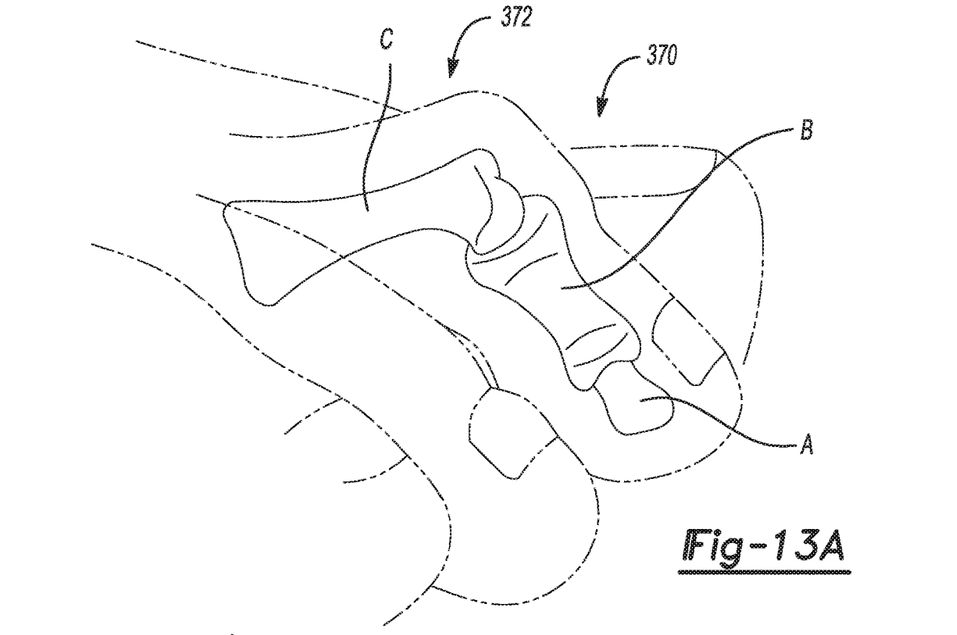
FIG. 13A is a partial lateral perspective view of a right human foot about to undergo a PIPJ arthrodesis procedure on the long toe in accordance with one example of the present disclosure.
Figures 13B, 13C:
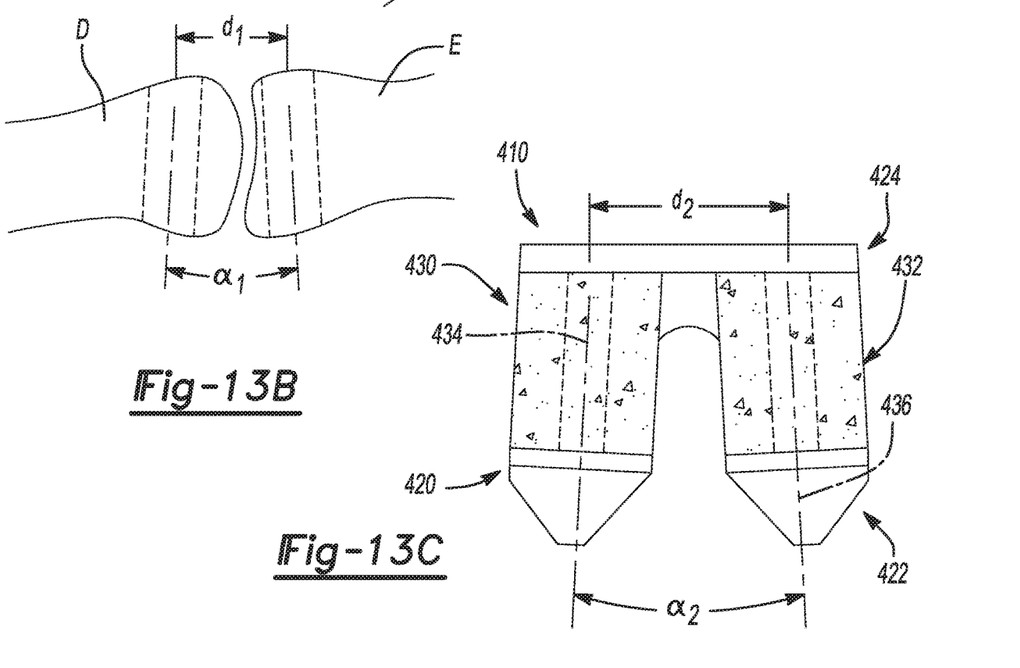
FIG. 13B is a lateral view of two bone segments.
FIG. 13C is a side view of another exemplary implant having bone interfacing portions that diverge.

Turning now to FIGS. 13A-14C, an exemplary PIPJ arthrodesis procedure using the implant 10 will be described. A partial lateral perspective view of a right human foot 370 about to undergo a PIPJ arthrodesis procedure on a long toe 372 is illustrated (FIG. 13A). The long toe 372 generally includes a distal phalange A, a proximal phalange B and a first metatarsal C. The example shown and described herein is directed toward fusion of the proximal phalange B and the first metatarsal C of the long toe 372. It will be appreciated however that the same may be applied to other adjacent bones in the toe or hand. FIG. 13B illustrates adjacent bone segments E and F. A distance d1 and a joint flexion angle $\alpha_1$ are defined between the phalanges E and F. FIG. 13C illustrates an implant 410 that includes an implant body 420 that extends longitudinally between an insertion end 422 and an opposite end 424. The implant body 420 further includes a first bone interfacing portion 430 and a second bone interfacing portion 432. The first bone interfacing portion 430 extends along a first bone engaging axis 434 and is configured to be implanted relative to a first phalange. The second bone interfacing portion 432 extends along a second bone engaging axis 436 and is configured to be implanted relative to a second phalange. The first and second axes 434 and 436 are diverging and define an angle $\alpha_2$. A distance d2 is defined between the first and second axes 434 and 436 at the opposite end 424. The first and second bone interfacing portions 430 and 432 are configured to be inserted dorsally, similar to the other examples disclosed herein, along the respective first and second bone engaging axes 434 and 436 and into the first and second phalanges, respectively. As will become appreciated herein, a distance or proximity of the phalanges E and F can be controlled by $d_1$ and $d_2$. Similarly, a joint flexion angle can be controlled by angles $\alpha_1$ and $\alpha_2$.

Figure 14A:
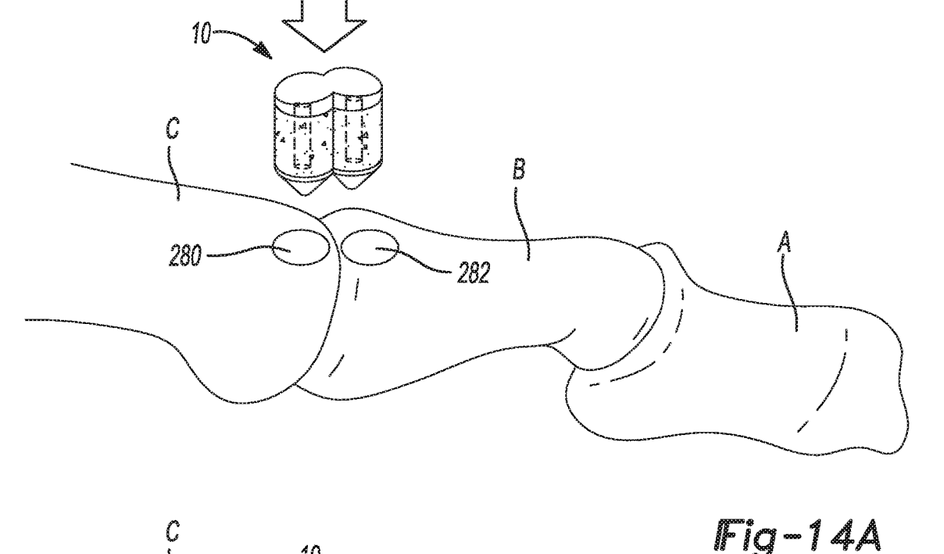
FIG. 14A is a lateral view of a long toe of the right foot shown in FIG. 13A including a distal phalange, proximal phalange and first metatarsal shown with a bone hole prepared into both of the proximal phalange and the first metatarsal for receipt of the implant shown in FIG. 1.
Figures 14B, 14C:
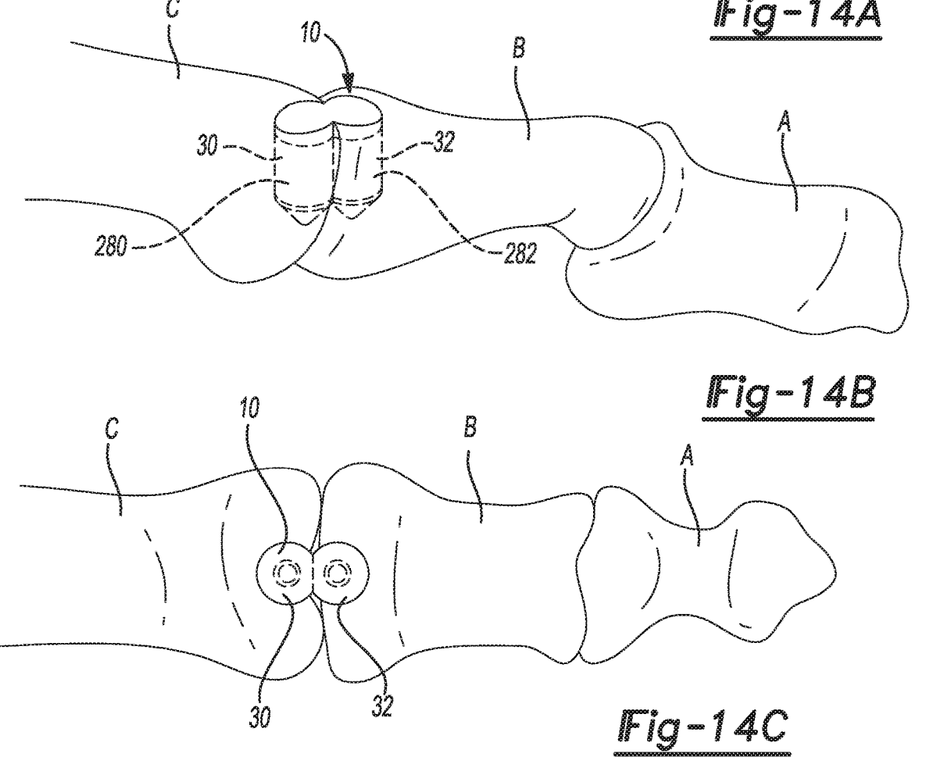
FIG. 14B is a lateral view of the long toe showing the implant of FIG. 1 implanted distally into the prepared bone holes in the proximal phalange and first metatarsal shown in FIG. 14A.
FIG. 14C is a superior view of the long toe and implant shown in 14B.

FIGS. 14A and 14B illustrate an exemplary sequence of implanting the implant 10 dorsally into a first bone hole 280 prepared in the proximal phalange A and a second bone hole 282 prepared in the first metatarsal C according to one example of the present disclosure. In one surgical method, minimal surrounding tissue of the proximal phalange B and the first metatarsal C at the PIPJ is removed. Because the implant 10 is implanted dorsally, only minimal amounts of tissue need to be disrupted as compared to a prior art implant that require significant manipulation of the proximal phalange B and the first metatarsal C to gain access to the IM canals of the proximal phalange B and the first metatarsal C.

Once the proximal phalange B and the first metatarsal C are oriented in a preferred (generally linear) orientation, bone holes 280 and 282 may be drilled into the respective proximal phalange B and the first metatarsal C (see FIG. 14A). The bone holes 280 and 282 can be generally parallel to match the axes 34 and 36 (FIG. 1). Next, the surgeon locates the first and second insertion portions 40 and 42 (see FIG. 1) onto the bone holes 280 and 282 and advances the first and second bone interfacing portions 30 and 32 of the implant 10 dorsally into the bone bones 280 and 282. In the implanted position, the proximal phalange B and the first metatarsal C are fused and the hammertoe deformation is corrected.

Figure 15A:
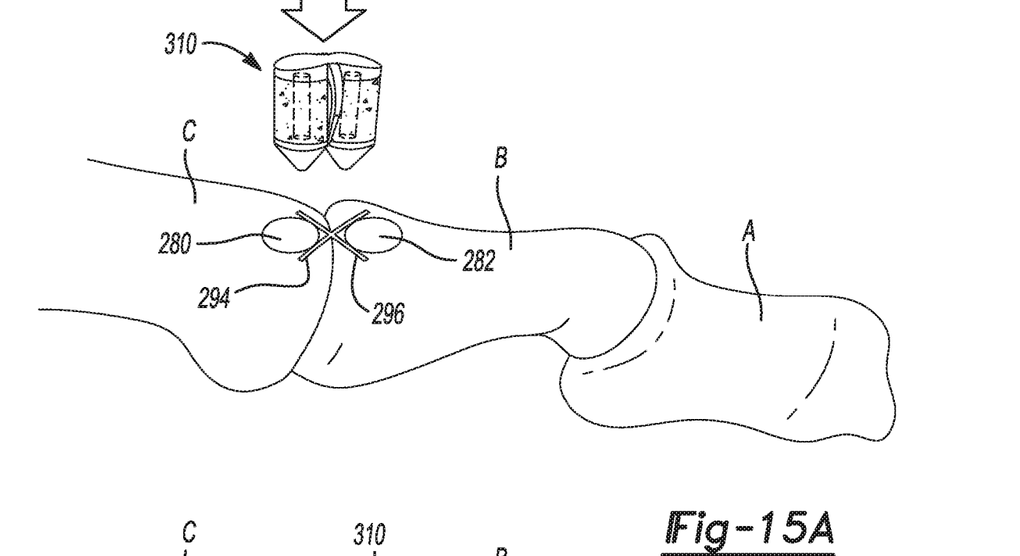
FIG. 15A is a lateral view of a long toe of the right foot shown in FIG. 13A including a distal phalange, proximal phalange and first metatarsal shown with a bone hole prepared into both of the proximal phalange and the first metatarsal for receipt of the implant shown in FIG. 10.
Figure 15B:
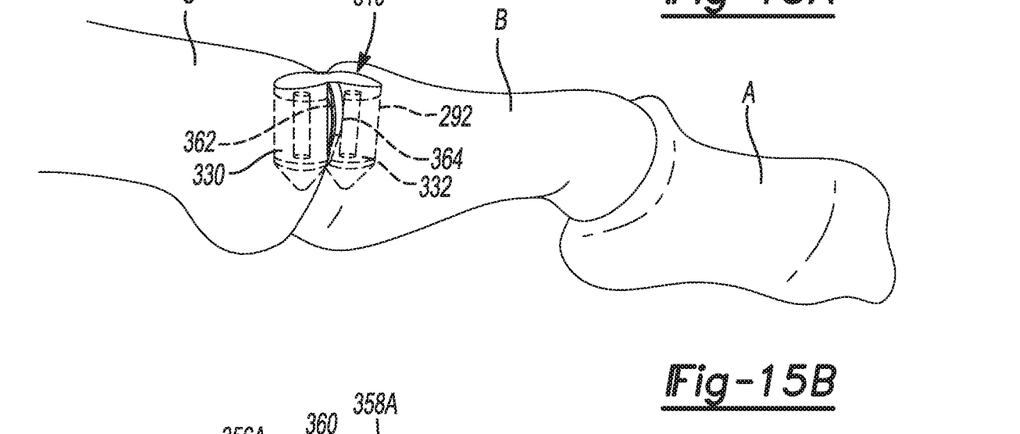
FIG. 15B is a lateral view of the long toe showing the implant of FIG. 10 implanted distally into the prepared bone holes in the proximal phalange and first metatarsal shown in FIG. 15A.
Figure 15C:
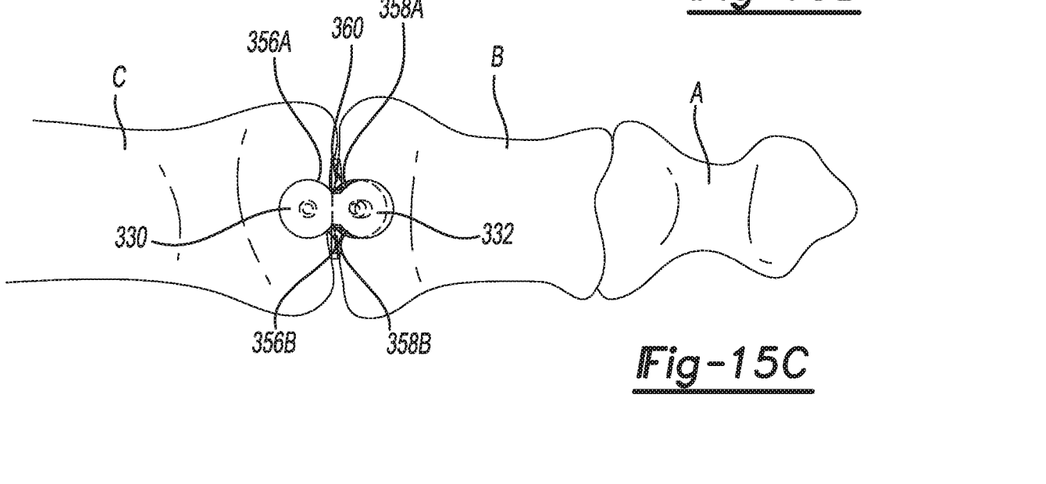
FIG. 15C is a superior view of the long toe and implant shown in 15B.

FIGS. 15A-15C illustrate a similar surgical procedure using the implant 310. Once the proximal phalange B and the first metatarsal C are oriented in a preferred (generally linear) orientation, bone holes 290 and 292 may be drilled into the respective proximal phalange B and the first metatarsal C (see FIG. 15A). The bone holes 290 and 292 can be generally parallel, or similar to the angle 366 to generally match the axes 334 and 336 (FIG. 11). In some examples the surgeon may prepare planar cuts 294 and 296 onto the proximal phalange B and first metatarsal C to match the profile of the planar surfaces 356A, 356B and 358A, 358C.

Next, the surgeon locates the first and second insertion portions 340 and 342 onto the bone holes 290 and 292 and advances the first and second bone interfacing portions 330 and 332 of the implant 310 dorsally into the bone bones 390 and 392. Notably, during the dorsal advancement, the planar surfaces 362 and 364 of the wedge 360 can slidably negotiate along the respective proximal phalange B and the first metatarsal C to further encourage proper alignment of the bone. In the implanted position, the proximal phalange B and the first metatarsal C are fused and the hammertoe deformation is corrected.

Figure 16:
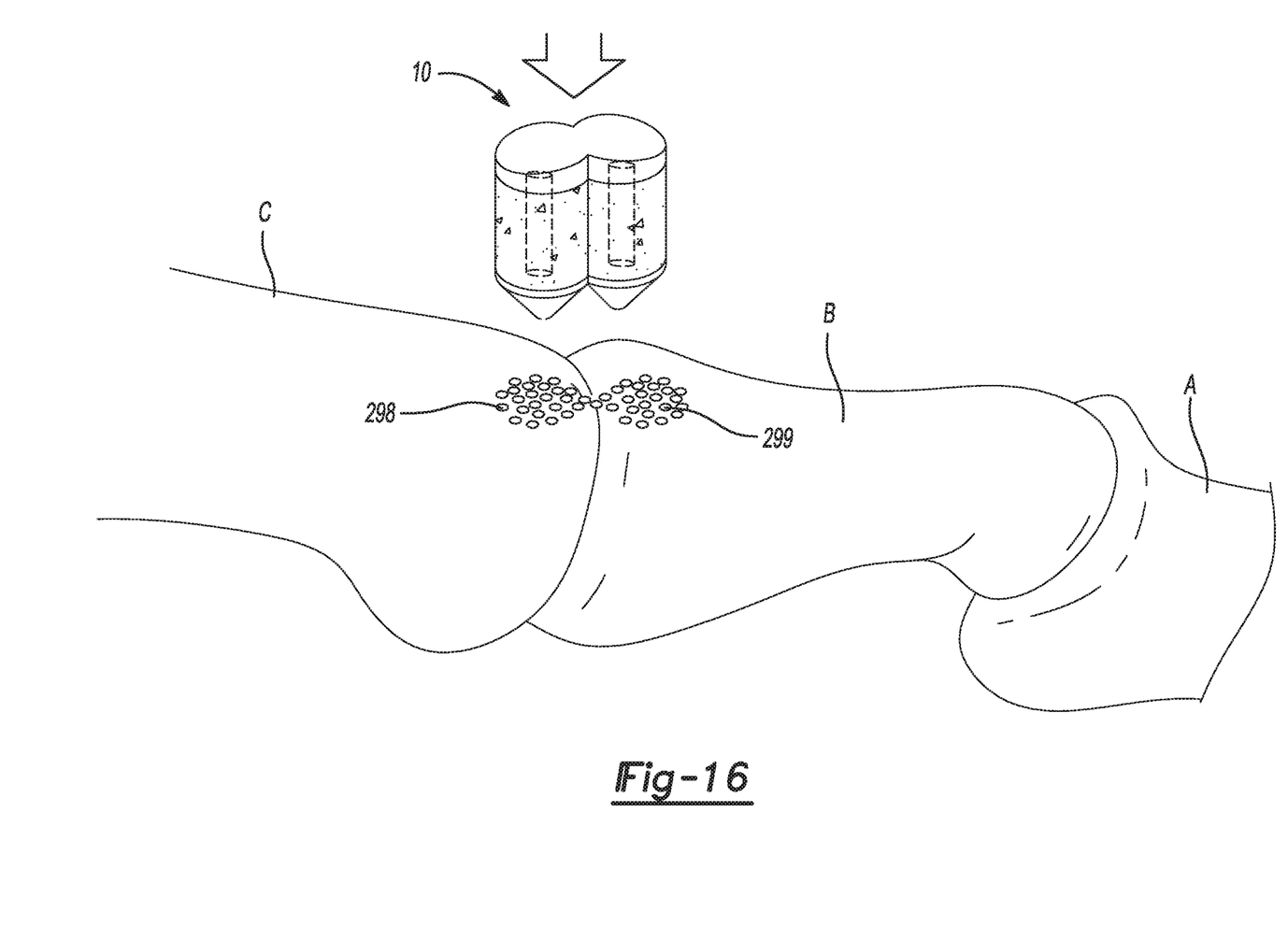
FIG. 16 is a lateral view of a long toe of the right foot shown in FIG. 13A including a distal phalange, proximal phalange and first metatarsal shown with a series of first bone holes prepared into the proximal phalange and a series of second bone holes prepared into the first metatarsal for receipt of an implant disclosed herein.

Turning now to FIG. 16, another surgical procedure according to the present disclosure will be described. In the previous examples, a single hole is described as being prepared into each phalange. In FIG. 16, a series of first holes 298 are prepared into the first metatarsal C. A series of second holes 299 are prepared into the proximal phalange B. As can be appreciated, several smaller diameter holes 298 and 299 may be prepared into the first metatarsal C and the proximal phalange B, respectively, to make up the larger overall shape of the desired implant.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An implant configured for fussing a first bone segment and a second adjacent bone segment during an operative procedure, the implant comprising:
    an implant core that extends along an implant axis between an insertion end and an opposite end, the implant core comprising:
    a first core portion comprising a first insertion portion and a first engagement portion; and
    a second core portion comprising a second insertion portion and a second engagement portion, the first engagement portion and the second engagement portion being coupled such that, in cross-section, the first engagement portion and the second engagement portion define a pair of intersecting shapes;
    a wedge extending outward from an intersected portion of the pair of intersecting shapes of the first engagement portion and the second engagement portion transverse to the implant axis and tapering towards the insertion end of the implant core; and
    a porous metal body matingly engaged with the implant core and extending along the implant axis between the first and second insertion portions and the first and second engagement portions of the implant core, respectively;
    the implant core, the wedge, and the porous metal body cooperatively defining a first bone engaging portion dorsally insertable into a bore disposed in the first bone segment and a second bone engaging portion dorsally insertable in a bore disposed in the second bone segment.

2. The implant of claim 1, wherein the wedge includes a first bone engaging face configured to engage the first bone segment and a second bone engaging face configured to engage the second bone segment, wherein the first bone engaging face and the second bone engaging face extend along converging planes.

3. The implant of claim 2, wherein the first bone engaging face and the second bone engaging face converge along the implant axis towards the insertion end of the implant core.

4. The implant of claim 2, wherein the first bone engaging face and the second bone engaging face converge to define an angle of about 10 degrees therebetween.

5. The implant of claim 2, wherein the first insertion portion tapers towards the insertion end of the implant core.

6. The implant of claim 5, wherein the first insertion portion is conical.

7. The implant of claim 5, wherein the second insertion portion tapers towards the insertion end of the implant core.

8. The implant of claim 7, wherein the second insertion portion is conical.

9. The implant of claim 2, wherein the first bone engaging portion extends along a first bone engaging axis and the second bone engaging portion extends along a second bone engaging axis.

10. The implant of claim 9, wherein the first bone engaging axis and the second bone engaging axis converge towards the insertion end.

11. The implant of claim 2, wherein the pair of intersecting shapes comprise two intersecting circles.

12. The implant of claim 2, wherein the implant core is solid.

13. The implant of claim 1, wherein the first insertion portion is disposed on a first end of a first connecting shaft and wherein the first engagement portion is disposed on a second end of the first connecting shaft, the first connecting shaft having a major cross-sectional dimension that is less than a major cross-sectional dimension of the first insertion portion and a major cross-sectional dimension of the first engagement portion.

14. The implant of claim 13, wherein the second insertion portion is disposed on a first end of a second connecting shaft and wherein the second engagement portion is disposed on a second end of the second connecting shaft, the second connecting shaft having a major cross-sectional dimension that is less than a major cross-sectional dimension of the second insertion portion and a major cross-sectional dimension of the second engagement portion.

15. An implant configured for fussing a first bone segment and a second adjacent bone segment during an operative procedure, the implant comprising:
    an implant core that extends along an implant axis between an insertion end and an opposite end, the implant core comprising:
    a first core portion comprising a first insertion portion disposed on a first end of a first connecting shaft and a first engagement portion disposed on a second end of the first connecting shaft, the first connecting shaft having a major cross-sectional dimension that is less than a major cross-sectional dimension of the first insertion portion and a major cross-sectional dimension of the first engagement portion; and
    a second core portion comprising a second insertion portion disposed on a first end of a second connecting shaft and a second engagement portion disposed on a second end of the second connecting shaft, the second connecting shaft having a major cross-sectional dimension that is less than a major cross-sectional dimension of the second insertion portion and a major cross-sectional dimension of the second engagement portion, the first engagement portion and the second engagement portion being coupled such that, in cross-section, the first engagement portion and the second engagement portion define a pair of intersecting shapes;

a wedge extending upward from an intersected portion of the pair of intersecting shapes of the first engagement portion and the second engagement portion transverse to the implant axis and tapering towards the insertion end of the implant core, the wedge including a first bone engaging face engageable with the first bone segment and a second bone engaging face engageable with the second bone segment, the first bone engaging face and the second bone engaging face extending along converging planes; and a porous metal body matingly engaged with the implant core and extending along the implant axis between the first and second insertion portions and the first and second engagement portions of the implant core, respectively;

the implant core, the wedge, and the porous metal body cooperatively defining a first bone engaging portion dorsally insertable into a bore disposed in the first bone segment and a second bone engaging portion dorsally insertable in a bore disposed in the second bone segment.

16. The implant of claim 15, wherein the first bone engaging face and the second bone engaging face converge along the implant axis towards the insertion end of the implant core.

\* \* \* \* \*